(12) United States Patent
Bosslet et al.

(10) Patent No.: US 8,552,159 B2
(45) Date of Patent: *Oct. 8, 2013

(54) BIFUNCTIONAL GLYCOPROTEINS HAVING A MODIFIED CARBOHYDRATE COMPLEMENT AND THEIR USE IN TUMOR-SELECTIVE THERAPY

(75) Inventors: Klaus Bosslet, Marburg (DE); Joerg Czech, Marburg (DE); Dieter Hoffmann, Marburg-Elnhausen (DE)

(73) Assignee: Behringwerke Aktiengesellschaft, Marburg (DE)

( * ) Notice: Subject to any disclaimer, the term of this patent is extended or adjusted under 35 U.S.C. 154(b) by 1005 days.

This patent is subject to a terminal disclaimer.

(21) Appl. No.: 10/815,925

(22) Filed: Apr. 2, 2004

(65) Prior Publication Data

US 2004/0202646 A1 Oct. 14, 2004

Related U.S. Application Data

(63) Continuation of application No. 09/302,434, filed on Apr. 30, 1999, now abandoned, which is a continuation of application No. 08/663,406, filed on Jun. 13, 1996, now abandoned, which is a continuation of application No. 08/235,395, filed on Apr. 29, 1994, now abandoned.

(30) Foreign Application Priority Data

May 4, 1993 (DE) .................................. P 43 14 556
Apr. 25, 1994 (EP) ...................................... 94106394

(51) Int. Cl.
*C07K 1/00* (2006.01)

(52) U.S. Cl.
USPC .......................................... 530/402; 514/21.2

(58) Field of Classification Search
None
See application file for complete search history.

(56) References Cited

U.S. PATENT DOCUMENTS 4,859,449 A * 8/1989 Mattes .......................... 424/1.49
5,135,736 A * 8/1992 Anderson et al. ............ 424/1.49
5,545,405 A * 8/1996 Page ........................... 424/133.1
5,632,990 A * 5/1997 Bagshawe et al. .......... 424/178.1
7,060,495 B2 * 6/2006 Gehrmann et al. ......... 424/94.61

FOREIGN PATENT DOCUMENTS

| CA | 2062047 | * | 8/1992 |
| EP | 0388151 | | 9/1990 |
| EP | 0 481 790 A2 | * | 4/1992 |
| EP | 0481790 | | 4/1992 |
| EP | 0501215 | | 9/1992 |
| EP | 0512905 | | 11/1992 |
| WO | WO 89/10140 | | 11/1989 |

OTHER PUBLICATIONS

Winkelhake (J. Biological Chemistry, 251(4): 1074-1080, 1976).*
Bosslet et al, Br. J. Cancer 65: 234-238, 1992.*
Jande et al, Cancer Res. 52: 6209-6215, 1992.*
Ponpipom et al. (J. Med. Chem. 1981, 24: 1388-1395).*
Day et al .(Journal of Biological Chemistry 1980; 255: 2360-2365).*
Hand et al., Comparative Biological Properties of a Recombinant Chimeric, Cancer Immunology Immunotherapy, vol. 35, 1992, pp. 165-174.
Kato et al., Activity Enhancement of a Lung Cancer-Associated Human Monoclonal Antibody HB4C5 by N Deglyocosylation, Human Antibodies and Hybridomas, vol. 4, No. 1, Jan. 1993, pp. 9-14.
Mattes, M., Biodistribution of Antibodies After Intraperitoneal or Intravenous Injection and Effect of Carbohydrate Modifications, J. of The National Cancer Institute, vol. 79, No. 4, 1987, pp. 855-864.

* cited by examiner

*Primary Examiner* — Laura B Goddard
*Assistant Examiner* — Meera Natarajan
(74) *Attorney, Agent, or Firm* — Lathrop & Gage LLP; James H. Velema, Esq.

(57) ABSTRACT

Provided herein are carbohydrate complement-modified bifunctional glycoproteins, and their use in tumor-selective therapy. The bifunctional glycoproteins comprise a first component that specifically binds to a tumor-specific antigen and a second component having enzymatic activity by means of which a non-toxic prodrug is cleaved into a cytotoxic drug. The carbohydrate complement comprises at least one exposed carbohydrate residue selected from the group consisting of mannose, galactose, N-acetylglucosamine, N-acetyllactose, glucose and fucose. The modified carbohydrate complement contributes to increased relative concentration of the glycoproteins at the site of the tumor, and enhanced clearance from the general circulation and non-tumor sites.

6 Claims, 8 Drawing Sheets

BIFUNCTIONAL GLYCOPROTEINS HAVING A MODIFIED CARBOHYDRATE COMPLEMENT AND THEIR USE IN TUMOR-SELECTIVE THERAPY

BACKGROUND OF THE INVENTION

1. Field of the Invention

The invention relates to bifunctional glycoproteins having targeting protein and enzyme properties. More particularly, the invention relates to such proteins whose complements of carbohydrate residues have been modified in a manner that enhances the clearance of such proteins from the circulation and increases the relative binding of the proteins at the tumor site. The enzymatic portion is capable of converting a prodrug into a cytotoxic drug that attacks tumor cells.

This invention also relates to the treatment of tumors with such proteins, and the production of such proteins, including recombinant production and production by transgenic animals.

2. Description of the Background Art

In efforts to control tumors, attempts have been made in the last twenty years to achieve selective therapeutic effects based on the specificity of antibodies. However, important therapeutic successes still have not been achieved in the case of solid tumors. Although highly specific tumor-selective monoclonal antibodies are available for targeting purposes, the lack of success in immunotherapy is primarily due to the small quantities of monoclonal antibody molecules that can be localized to solid tumors. One reason for this low degree of localization, which is generally insufficient for therapeutic purposes, is the presence of diffusion barriers in the tumor (Jain, R. K., Cancer Res. 47: 3039 (1987)). Prior attempts to compensate by increasing the dosage of the drug have encountered problems of widespread non-specific binding in non-tumor structures, and generalized toxic side effects.

Prior art compounds have sought to utilize (i) the specificity of a monoclonal antibody or tumor-binding protein partner and (ii) the catalytic amplification potential of an enzyme. Such antibody-enzyme conjugates can be administered to a patient and given time to bind to the tumor. Thereafter, a non-toxic prodrug, which can be cleaved by the enzyme portion of the conjugate to yield a cytotoxic drug, is administered to the patient. In theory, the enzyme portion of the molecules bound to the tumor converts the prodrug in the vicinity of the tumor into a drug which is cytotoxic to the tumor. In reality, however, such compounds suffer several drawbacks.

First, such antibody-enzyme conjugates are highly immunogenic in humans, since they represent chemical conjugates composed, as a rule, of mouse antibodies and xenogeneic enzymes. Repeated use of the same antibody-enzyme conjugate on the same patient is therefore not possible clinically (Bagshawe et al., Disease Markers, 9: 233 (1991)).

Second, the conjugates are only relatively slowly removed from the plasma, so that selective and effective prodrug activation is only possible if the elimination of the unwanted non-bound enzyme activity from the plasma is significantly enhanced.

The above-mentioned problem of the immunogenicity of xenogeneic antibody-enzyme conjugates is largely solved by using a recombinant fusion protein that is composed of purely human components. Details for the production of such fusion proteins are described in European Patent Application EP-A-0 501 215, which is incorporated by reference to the extent that it discloses such fusion proteins. In that publication, proteins are described, for example, of the general formula hutuMab-L-β-gluc, with hutuMab being a humanized, or human, tumor-specific monoclonal antibody, or a part thereof which still binds to the tumor, L representing a linker moiety, and β-gluc denoting human β-glucuronidase.

However, in carrying out pharmacological tests on such a fusion protein, it was unexpectedly found that, even at very short periods Cf time (1-3 minutes) after i.v. injection of the fusion protein into human tumor-carrying nude mice, significant quantities of the protein were bound to tumor cells in regions which are close to the blood vessels (easily accessible sites=EAS). Further, at these early times, large quantities of the fusion protein were still present in the plasma, so that selective and effective activation of a suitable prodrug in the tumor was not possible at this early time point after injection.

One proposed solution to the above problem is described in the International Patent Application WO 89/10140, which discloses a three component system for treatment of malignant diseases. The first component localizes at the tumor and has enzymatic activity, e.g., an antibody-enzyme conjugate. The second component is able to bind to the first component and inactivate the catalytic site and/or accelerate the clearance of the first component from the plasma. The third component is a prodrug which can be converted by the enzymatic activity of the first component to form the cytotoxic substance used to treat the tumor.

The three components of 89/10140 are designed to be administered sequentially, not simultaneously. That is, the first component is administered and given sufficient time to localize-at the tumor site. The second component is then administered after the first component has localized. Later, the third component is given.

The process of WO 89/10140 has drawbacks, however. First, it has the disadvantage of being a more complex process than the two step processes of the prior art. Moreover, by introducing an additional substance to the human or animal body, particularly the second compound, the risk of side effects and/or adverse reactions, such as the development of an unwanted immune reaction, is increased.

Accordingly, there remains a need for improved compounds and methods for selectively targeting tumors with cytotoxic drugs.

SUMMARY OF THE INVENTION

The present inventors have developed solutions to the foregoing problems that make it possible to achieve the desired therapeutic effects using a simpler, two step approach. In their investigation the present inventors prepared bifunctional compounds having both a tumor binding moiety and a catalytic moiety, which compounds are cleared very rapidly from the plasma. In doing so, it was expected that the incidence of binding to the tumor would be decreased due to the short time the compounds were in the plasma. Surprisingly, however, despite the very short presence of the compounds in the plasma, the relative binding of the compounds to the tumor increased. Moreover, to achieve the enhanced clearance, no additional compounds were administered either simultaneously with or subsequently to administration of the bifunctional compounds.

Thus, one aspect of the invention involves, in a first treatment step, administering intravenously ("i.v.") to tumor patients a compound comprising a bifunctional glycoprotein or bifunctional glycoprotein conjugate, the compound comprising a first portion that possesses an enzyme activity and a second portion that preferentially binds to a tumor-specific antigen. The carbohydrate complement of the compound comprises at least one exposed carbohydrate residue selected from the group consisting of mannose, galactose, N-acetylglucosamine, N-acetyllactose, glucose and fucose, which exposed residue is responsible for the advantageous binding and clearance characteristics of the compound. The enzyme activity of the first portion cleaves a non-toxic drug, which is administered to the subject either concurrently with or subsequently to the administration of the compound, to a form that is cytotoxic to the tumor cells.

For convenience, the term modified carbohydrate complement or the like will be used herein to denote a carbohydrate complement of the glycoprotein that comprises at least one exposed carbohydrate residue selected from the group consisting of mannose, galactose, N-acetylglucoseamine, N-acetyllactose, glucose and fucose.

Thus, in one aspect of the invention there is provided a bifunctional fusion glycoprotein ("FUP") containing a tumor targeting portion, an enzyme portion, and a modified carbohydrate complement. The modified carbohydrate complement contributes to an increased relative concentration of the FUP bound to a tumor and an enhanced clearance of the FUP from the general circulation and non-specific binding sites. The enzyme portion of the FUP is capable of cleaving a non-toxic drug into a tumor cytotoxic drug.

In another aspect of the invention, methods are provided for producing the FUPs having modified carbohydrate complements by colony selection, recombinant DNA and transgenic animal techniques, and chemical or enzymatic reactions.

In yet another aspect of the invention, a bifunctional antibody-enzyme conjugate ("AEC") having a modified carbohydrate complement is provided, wherein the antibody moiety is directed to an epitope on a tumor-specific antigen, and the enzyme is capable of converting a non-toxic drug into a tumor cytotoxic drug.

In still another aspect of the invention there are provided methods for appropriately modifying the carbohydrate complement of an AEC.

These and other aspects of the invention will become readily apparent by reference to the description of the invention and appended claims.

DETAILED DESCRIPTION OF THE FIGURES

FIG. 1 shows the amplification of the $V_H$ and $V_L$ genes. The $V_H$ gene, including its own signal sequence, is amplified (Güssow et al., *Meth. Enzymology*, 203: 99 (1991)) from pABstop 431/26 hum $V_H$ using the oligonucleotides pAB-Back and Linker-Anti (Table 1). The $V_L$ gene is amplified from pABstop 431/26 hum $V_L$ using the oligonucleotides Linker-Sense and $V_{L-(Mut)}$-For (Table 2).

Figure 6:
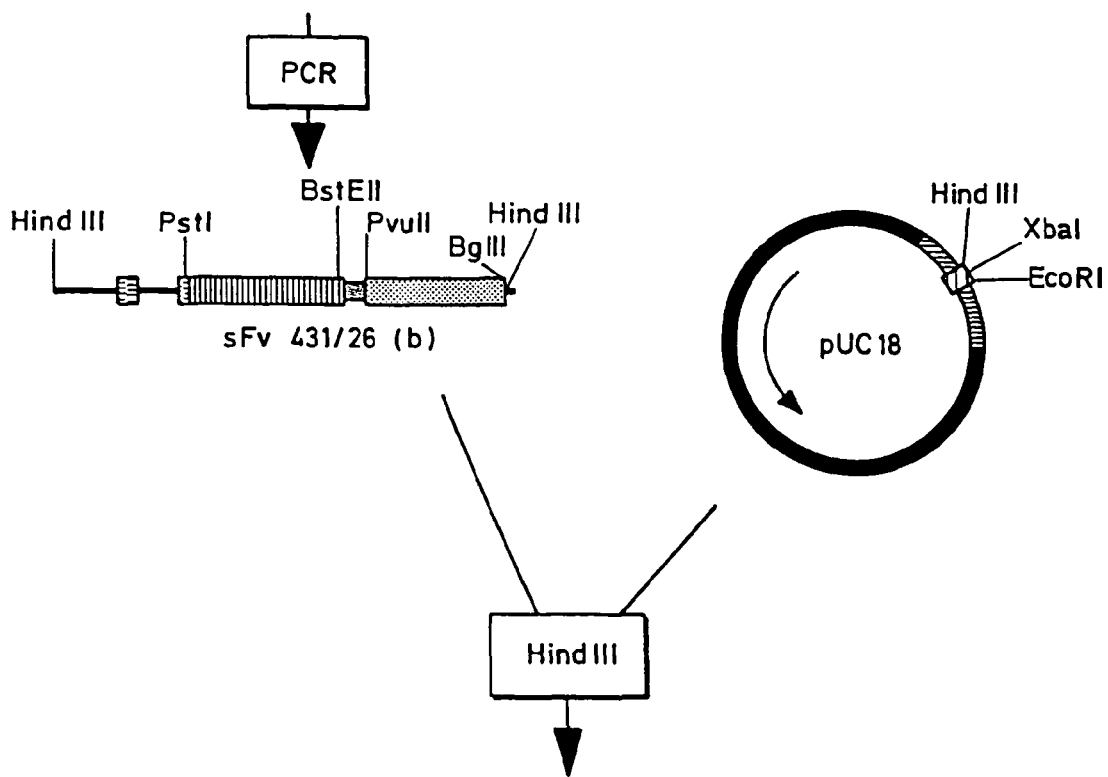

FIG. 6 shows the PCR amplification scheme. The sFv 431/26 fragment (a) is employed as the template for a PCR using the oligos pAB-Back (Table 2) and sFv-For (Table 5). This results in BgIII and HindIII cleavage sites being introduced at the 3' end of the newly generated sFv 431/26 fragment (b). The PCR fragment is purified and digested with HindIII, and then ligated into a pUC18 vector which has been cut with HindIII and treated with alkaline phosphatase. The plasmid clone pKBO1 is isolated, containing the sFv fragment with the BgIII cleavage site.

Figure 7:
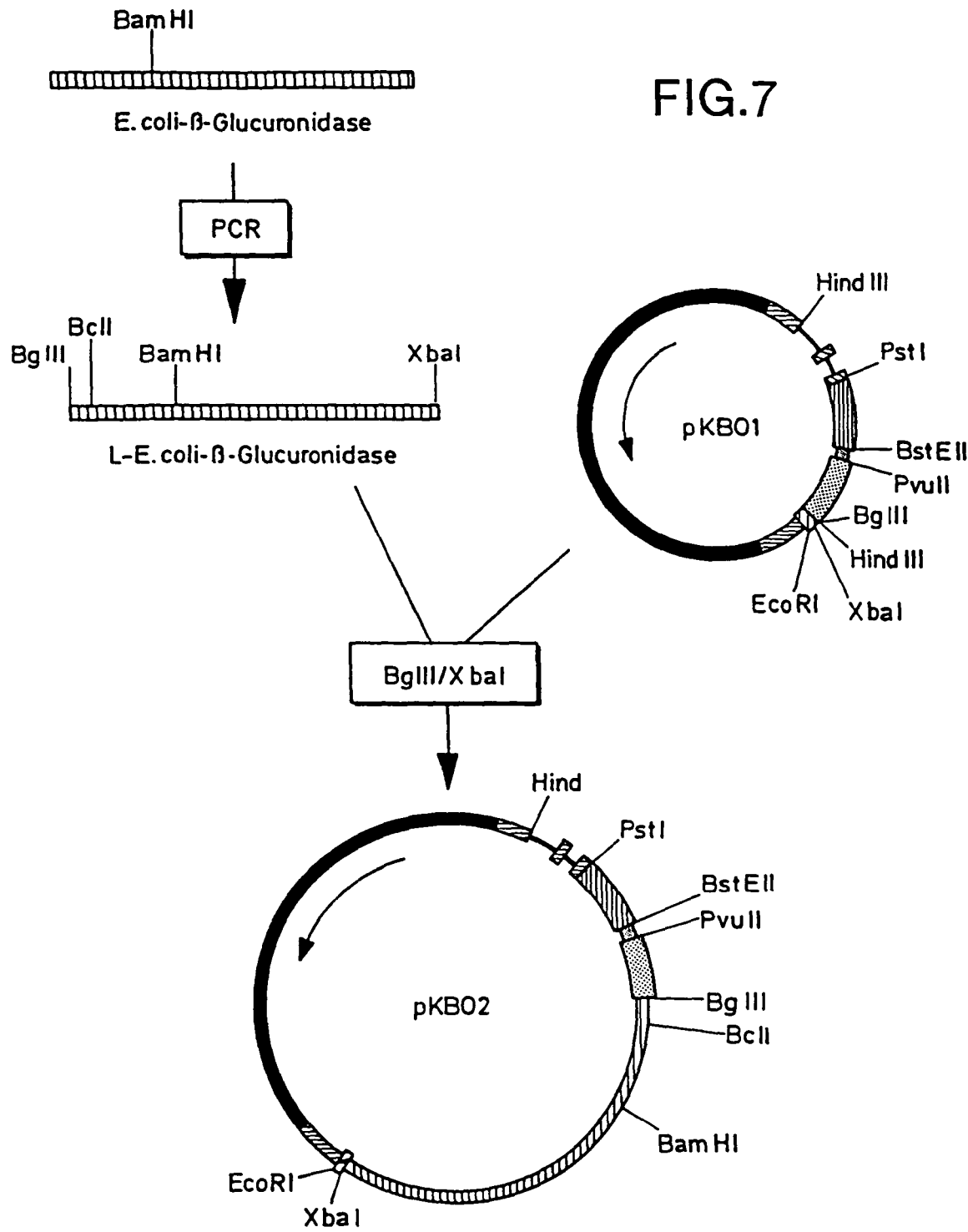

FIG. 7 shows the amplification of the gene encoding the *E. coli* β-glucuronidase from the vector pRAJ275 by PCR using the oligos *E. coli* β-gluc-Back1 (Table 6) and *E. coli* β-gluc.-For (Table 7), and at the same time provided with a BgIII cleavage site, an XbaI cleavage site and, at the 5' end, with a sequence encoding a linker. The resulting fragment is purified and digested with BgIII/XbaI, and then cloned into the vector pKBO1, which has likewise been digested with BgIII/XbaI. The plasmid clone pKBO2 is isolated, containing sFv 431/26 linked to the *E. coli* β-glucuronidase via a linker sequence.

Figure 8:
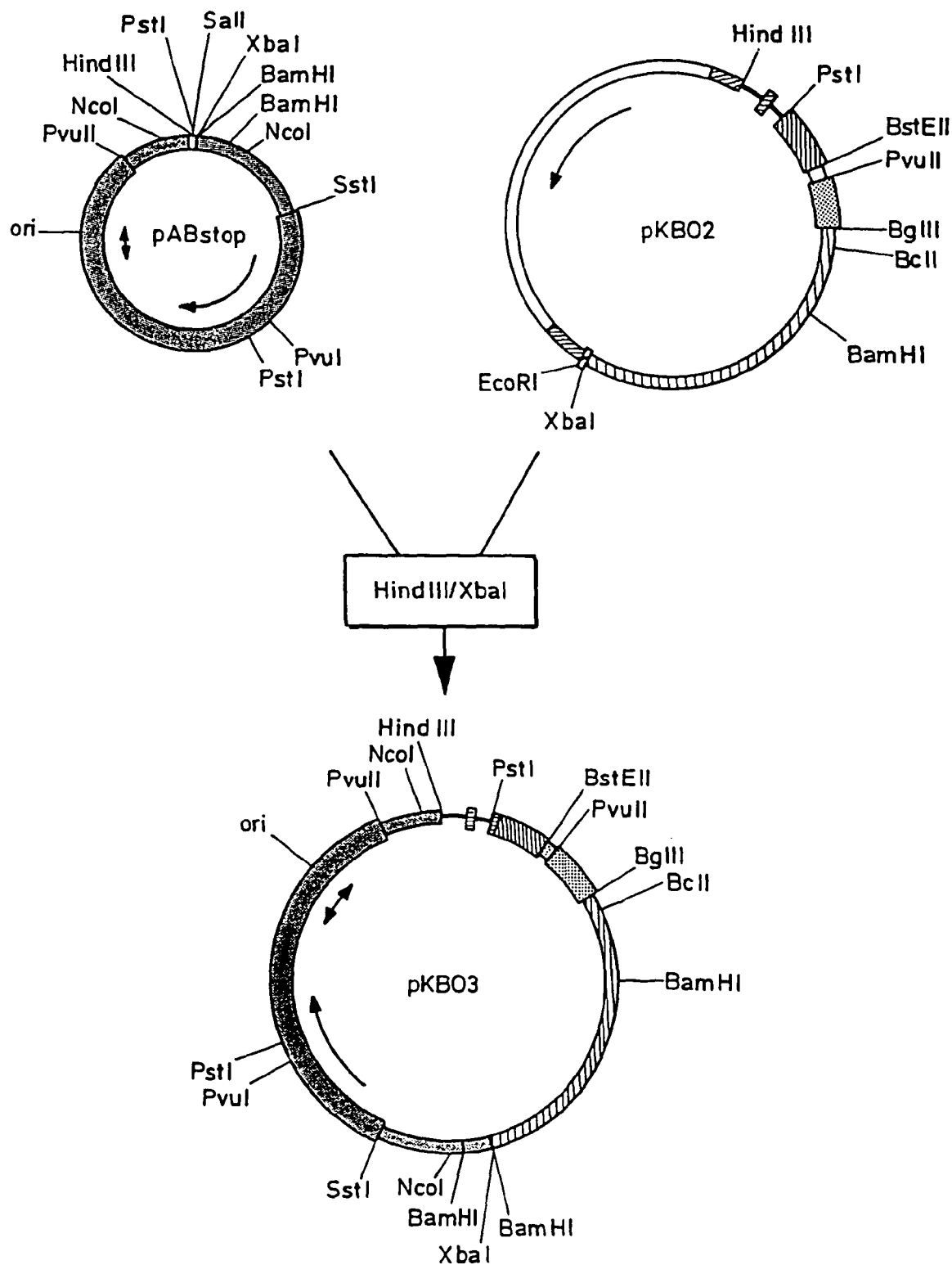

FIG. 8 shows the sFv-*E. coli* β-gluc. fragment, obtained from vector pKBO2 by digesting with HindIII/XbaI, is purified and then ligated into the expression vector pABstop, which has also been cut with HindIII/XbaI. The plasmid clone pKBO3 is isolated, containing the humanized sFv 431/26, a linker and the complete *E. coli* β-glucuronidase.

DETAILED DESCRIPTION OF THE INVENTION

It has been discovered that solid tumors in a subject may be treated efficiently in vivo with cytotoxic drugs, with no or lessened deleterious effect of the cytotoxic drugs on non-tumor tissues, by administering a carbohydrate complement-modified FUP or AEC of this invention with a prodrug. The targeting portion of the FUP or the targeting antibody of the AEC directs the fusion glycoprotein or glycoprotein conjugate to specific sites in or on a tumor cell, and the enzyme portion of the FUP or the AEC is capable of cleaving a prodrug to a tumor cytotoxic drug. As mentioned above, the modified carbohydrate complement enhances both the relative concentration of the FUP or AEC at the tumor site and increase the clearance of these proteins from non-specific sites and from the general circulation.

Once the FUP or AEC has been substantially cleared from the plasma and the normal tissues, while remaining bound on the tumor, a prodrug (advantageously hydrophilic), which is non-toxic and which disseminates extracellularly, is administered i.v. at appropriate (e.g., high) concentration. The prodrug is then cleaved by the FUP or AEC which is bound to the tumor to yield a tumor cytotoxic drug, which is advantageously lipophilic.

Glycoproteins are composed of oligosaccharide units linked to the protein chain(s) either through the side chain oxygen atom of serine or threonine by O-glycosidic linkages, or to the side chain nitrogen of asparagine residues by N-glycosidic linkages. The sum total of oligosaccharide units of a glycoprotein is referred to as the carbohydrate complement. The N-linked oligosaccharides contain a common pentasaccharide core consisting of 3 mannose (MAN) and 2 N-acetylglucoseamine (GlcNAc) residues, as shown in Sketch I (high mannose type) below.

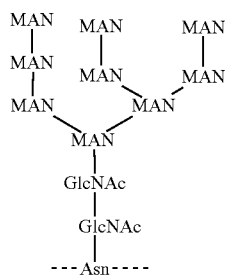

A complex type of oligosaccharide core is shown in Sketch II (see below), showing N-acetylneuraminic acid (sialic acid, SIA) residues as terminal carbohydrates, fucose (FUC) residues as side chains, and galactose (Gal) residues as penultimate sugars. Skilled artisans will appreciate that configurations other than those shown in sketches I and II are possible.

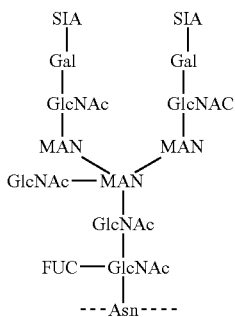

Additional sugars are attached to this common core in many different ways to form a great variety of oligosaccharide patterns. The nature of the terminal sugars in glycoproteins is part of a complex recognition system that is known to influence, inter alia, the uptake of glycoproteins by organs, macrophages and other tissues. See, e.g., Steer et al., *Prog. Liver Dis.*, 8:99 (1986); Stahl, *Curr. Opin. Immunol.*, 4: 49 (1992); Brady et al., *J. Inherit. Metab. Dis.*, in press (1994). These influences are highly tissue and glycoprotein specific, and it is not yet known a priori to predict patterns of enhanced clearance of particular circulating glycoproteins by specific tissues.

By galactosylating the FUP, or by eliminating terminal neuraminic acid residues from the protein by treating it with neuraminidase, the half life of the FUP in the plasma is shortened. It has been found, surprisingly, that the fusion protein which has been modified in this way continues to bind to the EAS, even at early time points, while retaining its specificity, avidity and enzymic activity. Further, the fusion protein is cleared from the plasma within 1-3 hours to such an extent that efficient, tumor-selective activation of a suitable prodrug is effectively made possible without the need to inject a clearing second antibody as in WO 89/10140 and Sharma et al., *Brit. J. Cancer* 61: 659 (1990). In addition, the present inventors have succeeded, by admixing, for example, galactose with the galactosylated FUP, in achieving still more efficient tumor localization. Further, it was possible successfully to extend these observations, within the scope of the invention, to additional FUPs and AECs, which were galactosylated or treated with neuraminidase, while preserving their biological properties.

Those skilled in the art will appreciate that different amounts of exposed residues may be utilized in the compounds of this invention. The number of exposed residues may be expressed as an average of exposed residues per molecule. For example, the average number of exposed residues per molecule generally will be at least about one, although averages of less than one are possible. Hence, for example, averages of less than 1, 1 to 2, 2 to 3, 3 to 4, 4 to 5, 5 to 6, 6 to 7, 7 to 8, 8 to 9, 9 to 10, 10 to 20, 20 to 50, 50 to 100, or greater than 100 are contemplated.

The general utility of the invention was verified using four different chemical compositions, namely, a xenogeneic antibody-enzyme conjugate, a humanized two-chain fusion protein, a humanized single-chain fusion protein and a xenogeneic single-chain fusion protein. Also useful are antibody fragment-enzyme conjugates, as well as to sFv-enzyme conjugates I and ligand-enzyme conjugates. The disclosure of WO 89/10140 is incorporated herein by reference to the extent that it discloses bifunctional proteins whose carbohydrate complement may be modified in accordance with this invention.

A representative AEC is composed of an intact monoclonal mouse antibody (e.g. as described in EP-A-0 388 914 which is incorporated by reference herein in its entirety) which is linked chemically to the enzyme *E. coli* glucuronidase by means of a heterobifunctional reagent according to Haisma et al. (*Brit. J. Cancer* 66: 474 (1992)) or to Wang et al. (*Cancer Res.* 52: 4484 (1992)), which are incorporated herein by reference in their entirety. Additional linkage possibilities, which can likewise lead to functional AECs, have been summarized by Means et al (*Bioconjugate Chem.* 1: 2 (1990), which is also incorporated by reference.

A humanized, two-chain fusion protein is described in detail in EP-A-0 501 215. It is a protein which is composed of two polypeptide chains and which has been prepared by genetic manipulation, one chain was prepared by linking the nucleotide sequences that encode a humanized $V_H C_{H1}$ hinge S region to the nucleotide sequence which encodes a human β-glucuronidase (S=oligonucleotide encoding a polypeptide spacer). Following transfection and expression in suitable expression systems, preferably BHK or CHO cells, the nucleotide sequence which encodes the humanized $V_L C_L$ chain, together with the above-mentioned nucleotide sequence, produces the humanized two-chain fusion protein.

The humanized single-chain fusion protein was produced, following expression in suitable expression systems, preferably in BHK or CHO cells, by linking the nucleotide sequences which encode the humanized $V_H S V_L$ hinge S region (single chain Fv, sFv) and the nucleotide sequence which encodes human β-glucuronidase. The construction of a representative humanized single-chain fusion protein is described in Examples 1-4 below. A xenogeneic single-chain fusion protein is described in Example 5 below.

After recloning into suitable vectors, the constructs which are described in the examples below can also be expressed in other expression systems, such as, for example, *E. coli, Saccharomyces cerevisiae* and *Hansenula polymorpha*, insect cells or transgenic animals.

Non-human transgenic mammalian animals can be genetically engineered to secrete into readily accessible body fluids such as milk, blood and urine recombinant human FUPs of the invention in amounts and in forms that are suitable for treating humans with tumors.

The term "animal" here denotes all mammalian animals except humans. It also includes an individual animal in all stages of development, including embryonic and fetal stages. A "transgenic" animal is any animal containing cells that bear genetic information received, directly or indirectly, by deliberate genetic manipulation at the subcellular level, such as by microinjection or infection with recombinant virus.

"Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the invention also contemplates the use of extrachromosomally replicating DNA sequences, such as might be engineered into yeast artificial chromosomes.

The term "germ cell line transgenic animal" refers to a transgenic animal in which the genetic information has been taken up and incorporated into a germ line cell, therefore conferring the ability to transfer the information to offspring. If such offspring, in fact, possess some or all of that information, then they, too, are transgenic animals.

The information to be introduced into the animal is preferably foreign to the species of animal to which the recipient belongs (i.e., "heterologous"), but the information may also be foreign only to the particular individual recipient, or genetic information already possessed by the recipient. In the last case, the introduced gene may be differently expressed than is the native gene.

The transgenic animals of this invention may be any, other than human, that produce milk, blood serum, and urine. Farm animals (pigs, goats, sheep, cows, horses, rabbits and the like), rodents (such as mice), and domestic pets (for example, cats and dogs) are included in the scope of this invention. It is preferred to select a transgenic animal that secrets into its milk a recombinant fusion protein, whose carbohydrate complement is modified to expose at least one mannose, galactose, N-acetylglucosamine, N-acetyllactose, glucose or fucose residue.

It is highly preferred that the transgenic animals of the present invention be produced by introducing into single cell embryos appropriate polynucleotides that encode the inventive FUPs in a manner such that these polynucleotides are stably integrated into the DNA of germ line cells of the mature animal and inherited in normal mendelian fashion.

Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal.

In a preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals. Those techniques as well known. For instance, reviews of standard laboratory procedures for microinjection of heterologous DNAs into mammalian fertilized ova include: Hogan et al., *Manipulating the Mouse Embryo*, Cold Spring Harbor Press, 1986; Krimpenfort et al., *Bio/Technology* 9: (1991); Palmiter et al., *Cell,* 41:343 (1985); Kraemer et al., *Genetic Manipulation of the Early Mammalian Embryo*, Cold Spring Harbor Laboratory Press, 1985; Hammer et al., *Nature,* 315:680 (1985); Meade et al., U.S. Pat. No. 4,873,316; Wagner et al., U.S. Pat. No. 5,175,385; Krimpenfort et al., U.S. Pat. No. 5,175,384, all of which are incorporated by reference in their entirety. The procedure of Meade et al., U.S. Pat. No. 4,873,316 is believe to provide one advantageous method of production, for example, using transgenic goats expressing the fusion protein under the control of the β-casein promoter in the mammary gland.

Genes for insertion into the genomes of transgenic animals so as to produce the FUPs of the invention can be obtained as described in the above-incorporated references and in the examples below. The gene encoding humanized two chain fusion glycoporteins are described in EP-A-0 501 215. The disclosure of which is incorporated herein by reference. The construction of a gene for a representative single-chain fusion glycoprotein is described in Examples 1-4 below. The gene for a single chain fusion glycoprotein is described in Example 5. Within the scope of the recombinantly produced modifications described herein, one can prepare constructs that include genes that encode proteins controlling posttranslational modification of expressed fusion glycoproteins. For example, constructs can be prepared, in which the sialyl transferase synthesis cycle is lacking or defective, thus producing fusion proteins in which terminal sialic acid residues are reduced in number or absent.

The cDNAs encoding desired FUPs can be fused, in proper reading frame, with appropriate regulatory signals to produce a genetic construct that is then amplified, for example, by preparation in a bacterial vector, according to conventional methods (see, Sambrook et al, *Molecular Cloning: A Laboratory Manual*, Cold Spring Harbor Press, 1989 which is incorporated herein by reference in its entirety). The amplified construct is thereafter excised from the vector and purified for use in producing transgenic animals. Purification can be accomplished by means of one or more cycles of anionic HPLC; alternate techniques include ultracentrifugation through a sucrose or NaCl gradient, gel electrolution followed by agarose treatment and ethanol precipitation, or low pressure chromatography. Purification by several cycles of HPLC allows for remarkably high transformation frequencies, on the order of 20% or more in both mice and pigs.

The regulatory signals referred to above include cis-acting signals necessary for mammary gland-specific expression of the fusion proteins and their post-translational glycosylation, secretion of the expressed fusion glycoprotein into milk or other body fluids, and expression of full biological activity.

Such regulatory signals include the promoter that drives expression of the fusion genes. Highly preferred are promoters that are specifically active in mammary gland cells and that involve milk proteins. Among such promoters, preferred are those for the whey acidic protein (WAP), short and long α, β and kappa caseins, α-lactalbumin and β-lactoglobulin (BLG) promoters.

Promoters may be selected on the basis of the native protein compositions of the various animals' milks. For example, the WAP and BLG promoters are particularly useful with transgenic rodents, pigs and sheep.

The genes for these promoters have been isolated and characterized. Clark et al., *TIBTECH* 5:20 (1987); Henninghausen, *Protein Expression and Purification* 1:3 (1990), which are incorporated by reference. The promoters can be isolated by conventional restriction endonuclease and subcloning steps. A mouse WAP promoter, isolated as a 2.6 kb EcoR1-Kpn1 fragment immediately 5' to the WAP signal sequence can be used, although the "long" WAP promoter (the 5' 4.2 kb Sau 3A-Kpn1 promoter of the mouse gene is also suitable.

Important to the transgenic animal embodiment are regulatory sequences that direct secretion of proteins into milk and/or other body fluids. Generally, homologous or heterologous regulators sequences known to direct the secretion of milk proteins, such as either signal peptides from milk or nascent target polypeptides, can be used, although the scope of this invention includes signal sequences that direct the secretion of proteins into fluids other than milk.

Among the useful sequences that regulate transcription, in addition to those described above, are enhancers, splice signals, transcription termination codons, and polyadenylation sites.

The injected DNA sequences may also include a 3' untranslated region downstream of the DNA encoding the desired fusion protein, or the milk protein gene used for regulation. This region may stabilize the RNA-transcript of the expression system and thus increase the yield of the desired fusion protein. Among these 3'untranslated regions useful in this regard are sequences that provide a poly A signal. Such sequences can be derived from, for example, the SV40 small t antigen, the casein 3' untranslated region, and others well known in this art.

Obtaining milk from transgenic female animals is done conventionally. McBurney et al., *J. Lab. Clin. Med.*, 64:485 (1964); Velander et al., *Proc Natl. Acad. Sci. USA* 89: 12003 (1992).

Within the scope of recombinantly produced modifications, there are employed those, for example, in which the gene for sialyl transferase is inactive or is lacking, or in which other enzymes of the sialyl transferase synthesis cycle are deficient or are lacking. Other preferred expression systems exhibit overexpression of galactosyl transferase or mannose-6-phosphate synthetases/transferases. In addition, it has been found that clones which have been produced from CHO cells having a very high ability to express fusion protein, for example, by means of double selection, in accordance with EP-A-0 330 977 (which is incorporated by reference herein in its entirety), are deficient in sialyation. Such clones, that may generally be produced by a process known as "homologous recombination" (Pomerantz et al., Progress in Cancer Res. and Therapy, 30:37-45 (1975), incorporated by reference herein in its entirety), are thus very suitable for use as expression systems.

These proteins (antibody-enzyme conjugate, humanized two-chain fusion protein, humanized single-chain fusion protein and xenogeneic single-chain fusion protein, which have been described by way of example), were, once they had been purified by anti-idiotype and/or anti-β-glucuronidase immunoaffinity chromatography, chemically galactosylated in accordance with the method described by Krantz et al. (*Biochemistry* 15: 3963 (1976) which is incorporated by reference herein in its entirety) or, alternatively, treated with carrier-bound neuraminidase. In that which follows, they are termed modified glycoproteins.

The modified proteins were compared in vitro and in vivo to the control unmodified starting proteins which had been expressed in BHK cells. The in vitro tests for specificity, affinity, quantitative immunoreactivity and quantitative enzyme activity demonstrated that the modified proteins did not differ significantly in these respects from the control proteins. In contrast, the half life (t½β) of the modified proteins in mouse and rat plasma (in vivo) was dramatically shortened (Tables 6, 7).

As a result of this dramatic shortening of the t/2β, at 1-3 hours after injecting the galactosylated proteins i.v. into tumor-bearing nude mice, modified proteins could no longer be detected in the plasma. In the case of the desialylated proteins, the t½β was shortened to such an extent that desialylated protein was no longer detectable in the plasma after 48 hours. At the same time, the concentration of functionally active modified proteins in the tumor was in the range from 200-400 ng/g of tumor (a very high specificity ratio>100:1 was consequently obtained on injecting≈400 μg of modified protein per mouse).

Viewed in absolute terms, the concentrations of modified proteins can be two to three times higher than those which are achieved, after appreciably longer times, for a comparable specificity ratio using unmodified starting proteins in vivo. Furthermore, the above-mentioned high specificity ratio (μg of modified protein/g of tumor:μg of modified protein/g of normal tissue) for modified proteins, is attained after only a few hours (1-3 hours or 48 hours, respectively), whereas, in the case of the unmodified starting proteins, a comparable specificity ratio (μg of unmodified starting protein/g of tumor: μg of unmodified starting protein/g of normal tissue) is only reached after several days (7-8 days), or even requires the use of a second antibody to accelerate the rate of clearance from normal tissue.

The rapid removal of the modified proteins from the plasma and the extracellular region of the organism by means of internalization via sugar-binding receptors (chiefly the galactose receptor in the liver, Thornburg et al., *J. Biol. Chem.* 255: 6820 (1980)) should also lead to the modified proteins having reduced immunogenicity in humans, particularly in the case of the antibody-enzyme conjugate and the xenogeneic single-chain fusion protein. This therefore also facilitates the use of xenogeneic or humanized FUPs in anti-tumor therapy, or at the least makes such use appear feasible for the first time.

A particularly useful humanized two-chain fusion protein has been expressed in CHO cells that had been selected for a very high level of expression, and purified by anti-idiotype affinity chromatography. Three or seven days after i.v. injection, this FUP was concentrated in the tumor to an extent 2-3-fold higher than that of the analogous fusion protein that is expressed in the BHK cells (Table 8). In addition, the FUP that has been expressed in CHO cells is removed from the plasma appreciably more efficiently than the fusion protein expressed in BHK cells, so that tumor: plasma ratios of >15 are reached by day 3 in the case of the CHO fusion protein. In the case of the BHK fusion protein, the corresponding ratios are <1 (Table 8). On day 7, the tumor:plasma ratios for the CHO fusion protein are in the region of 130 while those for the BHK fusion protein are in the region of 20 (Table 8).

These highly significant pharmacokinetic differences between the humanized two-chain fusion protein expressed in CHO cells or expressed in BHK cells can be explained by differences in the carbohydrate content of the fusion proteins. An analysis of the monosaccharide components in the carbohydrate content of the fusion protein expressed in BHK or CHO cells is given in Table 1a. Differences are observed mainly in the content of galactose, mannose and N-acetyl-neuraminic acid.

TABLE 1a

An analysis of the monosaccharide components in the carbohydrate content of the fusion proteins
mol monosaccharide/mol fusion protein monomer (125 kDa)

| | Fucose | N-acetyl glucosamine | Galactose | Mannose | N-acetyl neuraminic acid |
|---|---|---|---|---|---|
| CHO fusion protein | 0.6 | 4.35 | 1.40 | 7.04 | 0.54 |
| BHK fusion protein | 0.68 | 4.46 | 1.59 | 6.31 | 0.69 |

Method:

Neuraminic acid was determined by the method of Hermentin and Seidat (1991) GBF Monographs Volume 15, pp. 185-188 (after hydrolysis of 30 min in the presence of 0.1 N sulfuric acid at 80° C. and a subsequent neutralization with 0.4 N sodium hydroxide solution) by high-pH anion exchange chromatography with pulsed amperometric detection (HPAE-PAD).

The monosaccharide components were determined (after hydrolysis of 4 h in the presence of 2 N trifluoracetic acid at 100° C. and evaporation to dryness in a SpeedVac) likewise by HPAE-PAD in a motivation of the method described by Hardy et al. (1988) Analytical Biochemistry 170, pp. 54-62.

Particularly, the increased amounts of mannose or mannose-6-phosphate in combination with reduced amounts of N-acetylneuraminic acid, as observed in the fusion protein expressed in CHO cells, might be responsible for its faster elimination from plasma and normal tissues due to more efficient binding to mannose and galactose receptors (compare Table 8, pharmacokinetics of unmodified fusion proteins). Furthermore, glycan mapping showed higher contents of high mannose/asialo-structures (see Sketch II above) in the CHO-expression product compared to the normal BHK-expression product.

The high β-glucuronidase concentrations, which were determined in the enzyme activity test, represent the activity of the endogenous murine β-glucuronidase and that of the FUP, as well as that of any human β-glucuronidase which may have been liberated from the latter by the cleavage which can potentially occur. Using enzyme-histochemical methods (Murray et al., *J. Histochem. Cytochem.* 37: 643 (1989)), it was demonstrated that this enzyme activity was present as intracellular activity in the normal tissues. Thus, this catalytic potential either does not contribute, or only contributes unimportantly, to the cleavage of a hydrophilic prodrug which is disseminated extracellularly.

The several embodiments exemplified below are not to be taken as in any way limiting the scope of the invention which is described in the specification and in the appended claims.

EXAMPLES

Examples 1-4

Recombinant preparation of a humanized single-chain fusion protein from a humanized tumor antibody moiety and human β-glucuronidase.

Example 1

Figure 1:
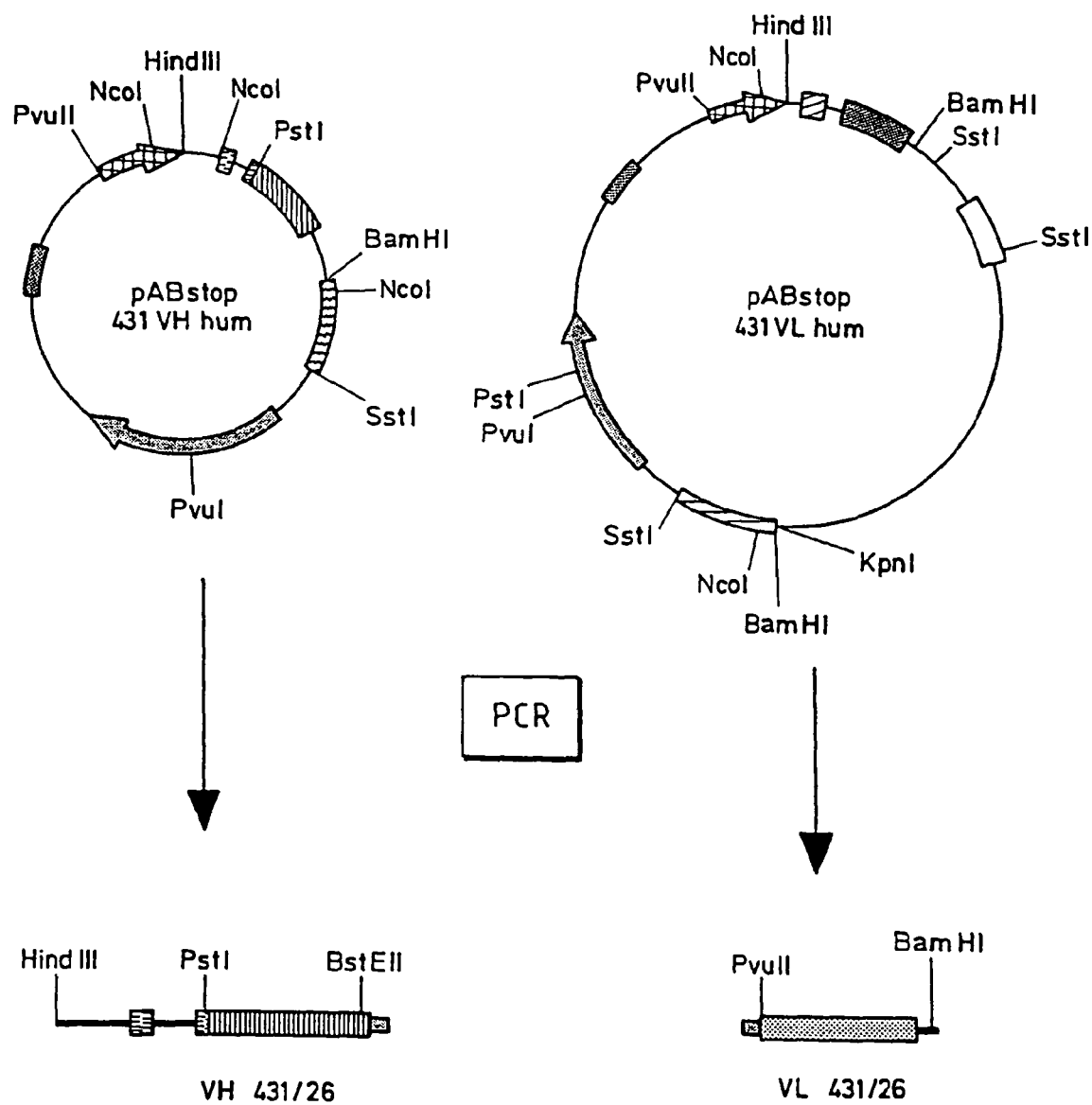
Figure 2:
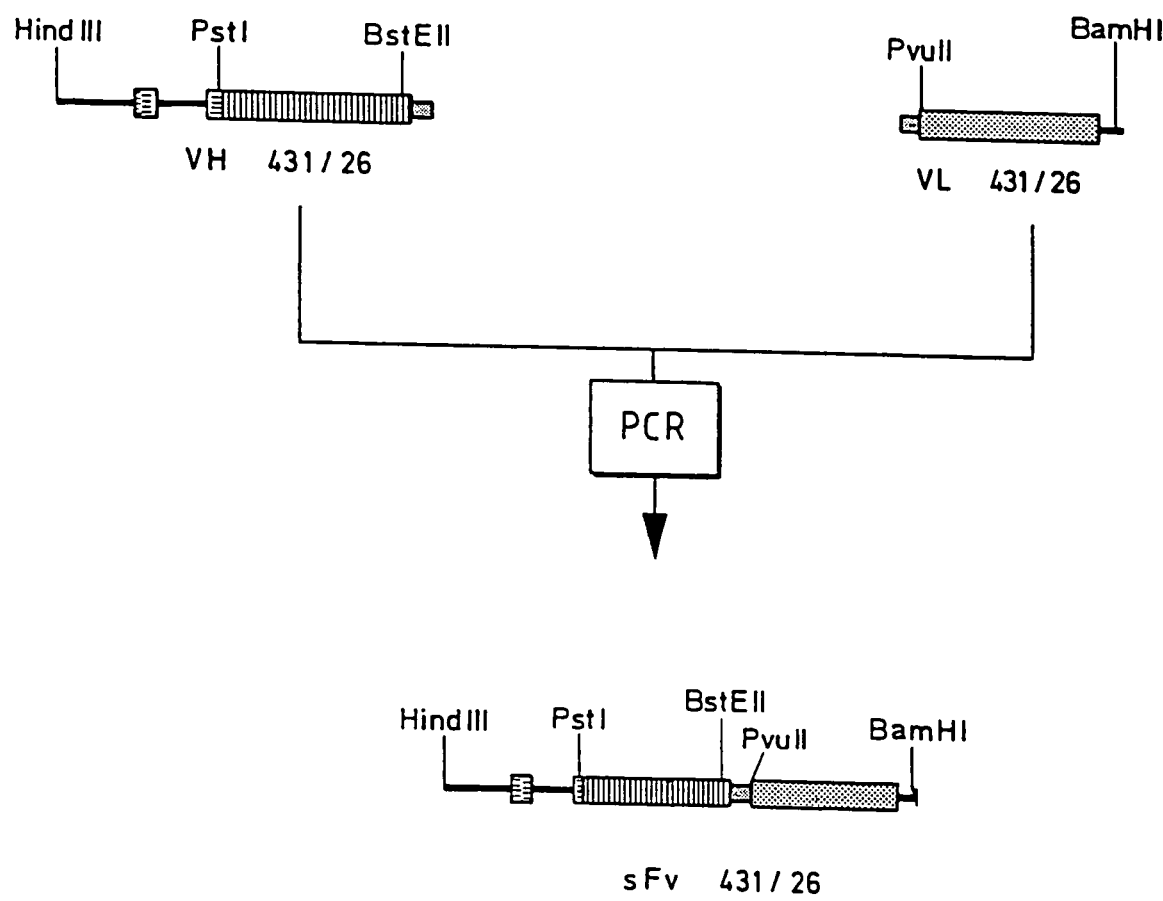
FIG. 2 shows a PCR fragment composed of the $V_H$ that is connected to the $V_L$ gene via a linker.

Using the oligonucleotides pAB-Back and Linker-Anti (Table 1), the $V_H$ gene, including its own signal sequence, is amplified from pABstop 431/26 hum $V_H$ (Güssow et al, 1991, above). Using the oligonucleotides Linker-Sense and $V_L$(Mut)-For (Table 2), the $V_L$ gene is amplified (FIG. 1) from pABstop 431/26 hum $V_L$ (Güssow et al., 1991, above).

TABLE 1 pAB-Back: SEQUENCE ID NO. 1
5'                                             3'
ACC AGA AGC TTA TGA ATA TGC AAA TC Linker-Anti: SEQUENCE ID NO. 2
5'
GCC ACC CGA CCC ACC ACC GCC CGA TCC ACC GCC TCC
                                             3'
TGA GGA GAC GGT GAC CGT GGT C

TABLE 2

Linker-Sense: SEQUENCE ID NO. 3
5'
GGT GGA TCG GGC GGT GGT GGG TCG GGT GGC GGC GGA
                                             3'
TCT GAC ATC CAG CTG ACC CAG AGC VL (Mut)-For: SEQUENCE ID NO. 4
5'
TGC AGG ATC CAA CTG AGG AAG CAA AGT TTA AAT TCT
                                             3'
ACT CAC CTT TGA TC Example 2

The oligonucleotides Linker-Anti and Linker-Sense are partially complementary to each other and encode a polypeptide linker which is intended to link the $V_H$ and $V_L$ domains to form an sFv fragment. In order to fuse the amplified $V_H$ and $V_L$ fragments, they are purified and introduced into a 10-cycle reaction as follows:

| | |
|---|---|
| $H_2O$: | 37.5 µl |
| dNTP's (2.5 mM) | 5.0 µl |
| PCR buffer (10×) | 5.0 µl |
| Taq polymerase (Perkin-Elmer Corp., Emmeryville, CA) (2.5 U/µl) | 0.5 µl |
| 0.5 µg/pl DNA of the $V_L$ frag. | 1.0 µl |
| 0.5 µg/pi DNA of the $V_H$ frag. | 1.0 µl |

PCR buffer (10×): 100 mM Tris, pH 8.3, 500 mM KCl, 15 m $MgCl_2$, 0.1% (w/v) gelatin.

Figure 4:
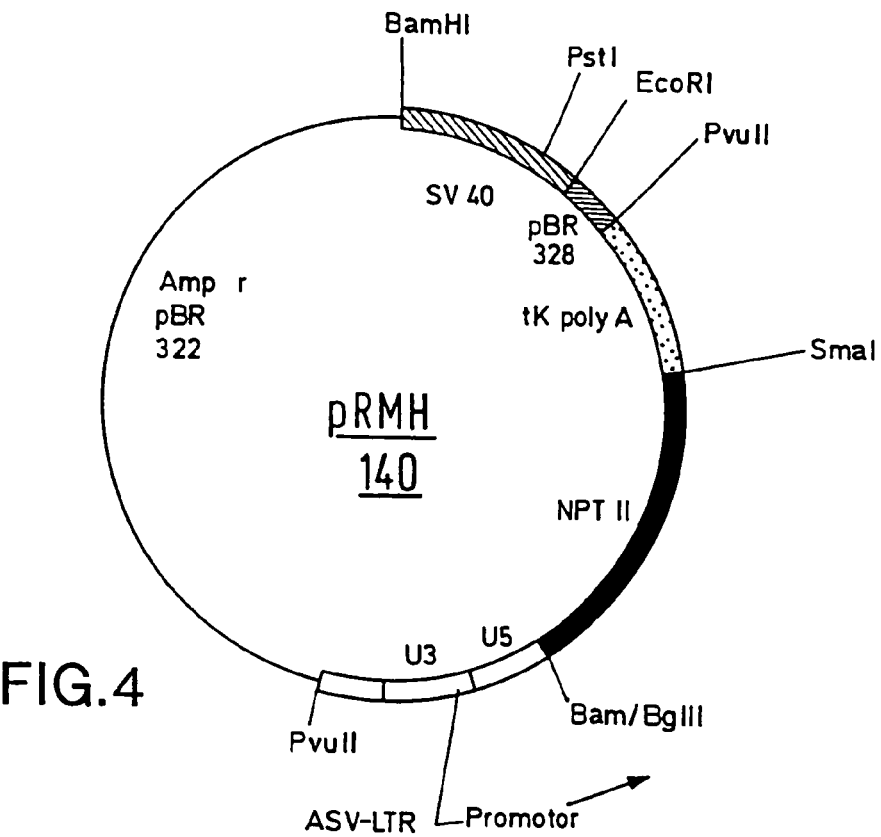
FIG. 4 shows the plasmid pRMH 140 that carries a neomycin resistance gene into transfected BHK cells.

The surface of the reaction mixture is sealed off with paraffin and the 10-cycle reaction is subsequently carried out in a PCR apparatus using the program 94° C., 1 min; 55° C., 1 min; 72° C., 2 min. After that, 2.5 pM of the flanking primers pAB-Back and $V_L$(Mut)-For are added and a further 20 cycles are carried out. A PCR fragment is obtained which is composed of the $V_H$ gene, which is connected to the $V_L$ gene via a linker (FIG. 4). The $V_H$ gene's own signal sequence is also located prior to the $V_H$ gene. As a result of using the oligonucleotide $V_L$(Mut)-For, the last nucleotide base of the $V_L$ gene, a C, is at the same time replaced by a G. This PCR fragment encodes a humanized single-chain Fv (sFv).

Example 3

Figure 3A:
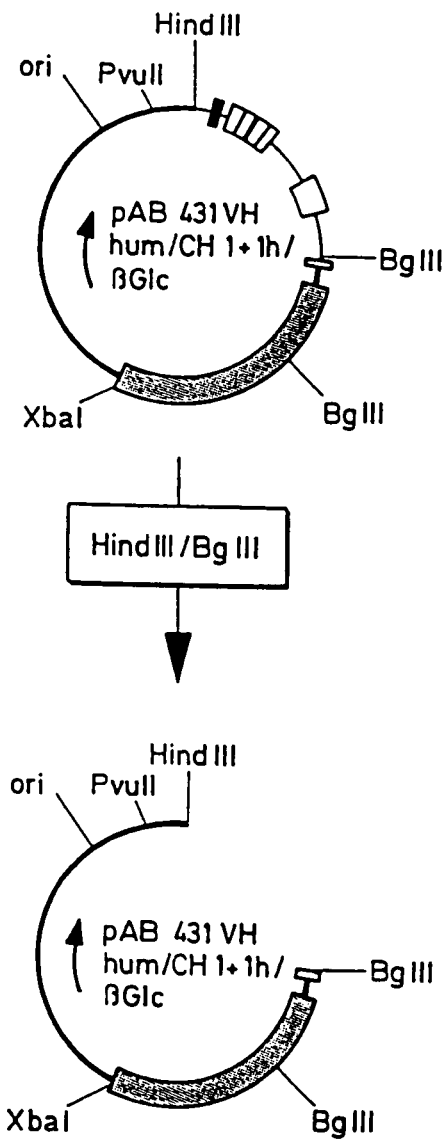
FIG. 3a shows the removal of the Hind III to Bglll restriction fragment from the plasmid pAB 431 VH to produce a vector.
Figure 3B:
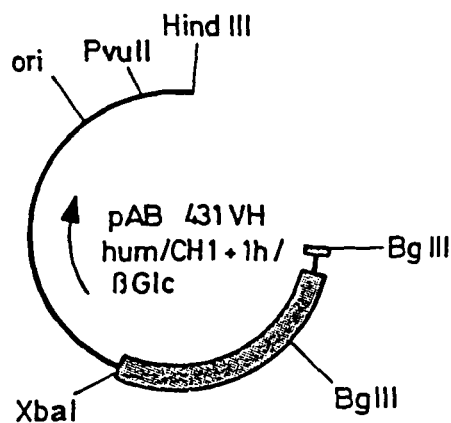
FIG. 3b shows the insertion of the PCR fragment from FIG. 2 into the vector from FIG. 3A to produce the plasmid pMCG-E1, which clone contains the humanized sFv 431/26, a hinge exon, and the complete β-glucuronidase, which clone is transfected into BHK cells.
Figure 3B:
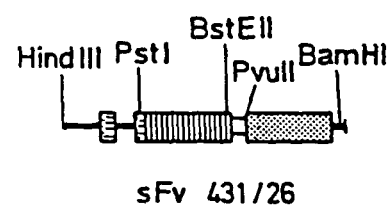
Figure 3B:
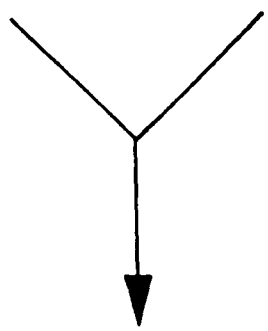
Figure 3B:
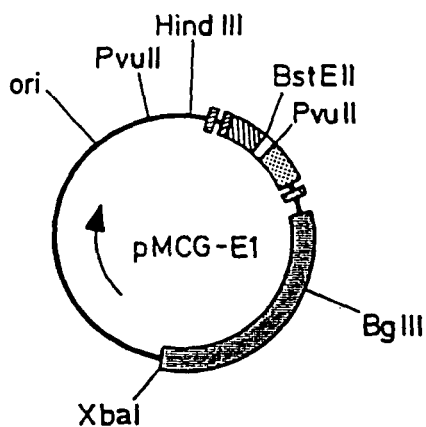

The sFv fragment from Example 2 is restricted with HindIII and BamHI and ligated into the vector pABstop 431/26$V_H$huβgluc1H, which has been completely cleaved with HindIII and partially cleaved with BgIII. The vector pABstop 1/26$V_H$huβgluc1H contains a $V_H$ exon, including the $V_H$-specific signal sequence, followed by a CH1 exon, the hinge exon of a human IgG3 C gene and the complete cDNA of human β-glucuronidase. The plasmid clone pMCG-E1 is isolated, which clone contains the humanized sFv 431/26, a hinge exon and the complete β-glucuronidase (FIG. 3a). Vector pABstop 431/26$V_H$huβgluc is described in Bosslet et al., *Brit. J. Cancer* 65: 234 (1992), which is incorporated by reference herein in its entirety and where information on the remaining individual components can be obtained from the references listed therein.

Example 4

Figure 5:
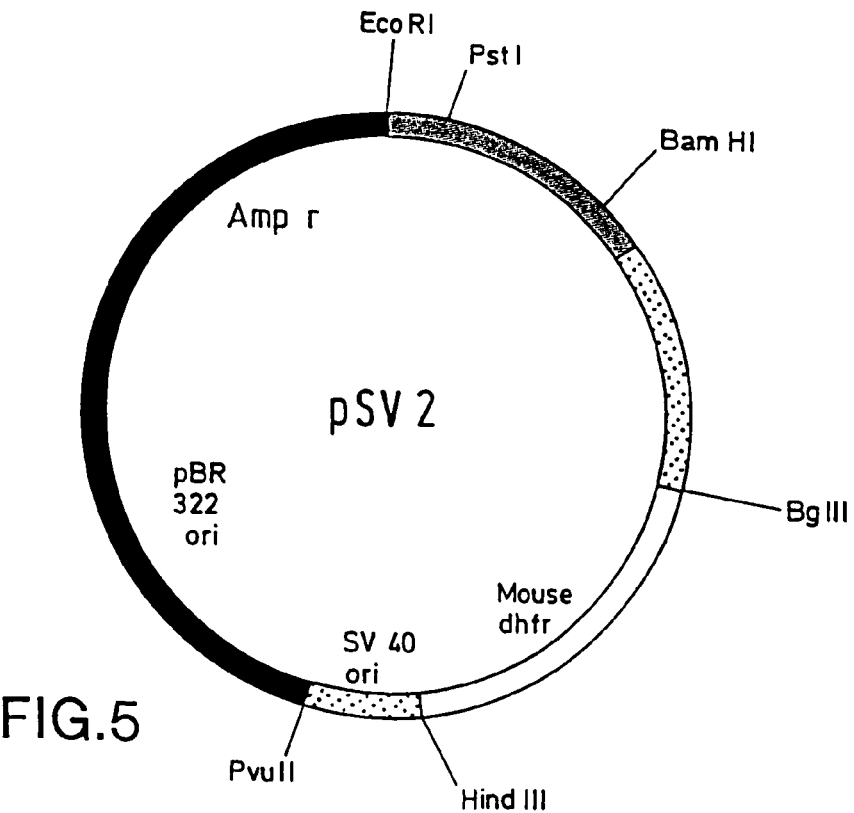
FIG. 5 shows the plasmid pSV2 that carries the methotrexate resistance gene into transfected BHK cells.

The clone pMCG-E1 is transfected, together with the plasmid pRMH 140 (FIG. 4), which carries a neomycin resistance gene, and the plasmid pSV2 (FIG. 5), which carries a methotrexate resistance gene, into BHK cells. The BHK cells then express a fusion protein which possesses both the antigen-binding properties of Mab BW 431/26hum and the enzymic activity of human β-glucuronidase (see Examples 8 and 9).

Example 5

Construction of Xenogeneic Single-Chain Fusion Protein

The xenogeneic single-chain fusion protein was produced, following expression in suitable expression systems, preferably in BHK cells, by linking the nucleotide sequences which encode the humanized $V_H$, S, $V_L$ hinge and S regions (see Examples 1-4 and below) to the nucleotide sequence which encodes E. coli β-glucuronidase. The construction of a single-chain fusion protein from a humanized sFv (antiCEA) and E. coli β-glucuronidase is described in detail below.

The sFv 431/26 fragment (a) is employed as the template for a PCR using the oligos pAB-Back (Table 1) and sFv-For (Table 3). In this way, BglII and HindIII cleavage sites are introduced at the 3' end of the newly generated sFv 431/26 fragment (b). The PCR fragment is purified and digested with HindIII, and then ligated into a pUC18 vector which has been cut with HindIII and treated with alkaline phosphatase. The plasmid clone pKBO1 is isolated, containing the sFv fragment with the BglII cleavage site (FIG. 6).

The gene encoding the E. coli (β-glucuronidase is amplified from the vector pRAJ260 (Jefferson et al., Proc. Natl. Acad. Sci. USA, 83:8447 (1986)) by PCR using the oligos E. coli (β-gluc-Back1 (Table 4) and E. coli β-gluc-For (Table 5), and at the same time provided at the 5' end with a BglII cleavage site, at the 3' end with an XbaI cleavage site and, additionally at the 5' end, with a sequence encoding a linker. The resulting fragment is purified and digested with BglII/XbaI, and then cloned into the vector pKBO1 which has likewise been digested with BglII/XbaI. The plasmid clone pKBO2 is isolated, containing sFv 431/26 linked to E. coli β-glucuronidase via a linker sequence (FIG. 7).

The sFv-E. coli β-gluc. fragment, obtained from vector pKBO2 by HindIII/XbaI digestion, is purified and then ligated into the expression vector pABstop (Zettlmeissl et al., *Behring Institute Mitteilungen* (*Communications*) 82: 26 (1988)) which has likewise been cut with HindIII/XbaI. The plasmid clone pKBO3 is isolated, containing the humanized sFv 431/26, a linker and the complete E. coli β-glucuronidase (FIG. 8).

TABLE 3 sFv For: SEQUENCE ID NO. 5
5'                                              3'
TTT TTA AGC TTA GAT CTC CAC CTT GGT C

TABLE 4

E. coli β-gluc-Back 1: SEQUENCE ID NO. 6
5'
AAA AAG ATC TCC GCG TCT GGC GGG CCA CAG TTA CGT
                     3'
GTA GAA ACC CCA

TABLE 5

E. coli β-gluc-For: SEQUENCE ID NO. 7
5'                                              3'
GCT TCT AGA TCA TTG TTT GCC TCC CTG

TABLE 6

Pharmacokinetic comparison between unmodified and modified humanized two-chain fusion proteins in CD-1 nude mice bearing a human tumor xenograft (MzSto1)

| | unmodified fusion protein produced in BHK cells | | | | | | | | | | | | | | |
|---|---|---|---|---|---|---|---|---|---|---|---|---|---|---|---|
| | μg fusion protein/g of tumor or/g of organ measured in an OFAT | | | | | | | | μg of β-glucuronidase/g of tumor or/g of organ measured in an EAT | | | | | | |
| | tumor | spleen | liver | intestine | kidney | lung | heart | plasma | tumor | spleen | liver | gut | kidney | lung | heart | plasma |
| 0.05 hr | 3 | 21 | 61.4 | 6.5 | 35.6 | 77.6 | 60.1 | 456.2 | n.d. | 48.5 | 81.7 | 18.6 | 45 | 83.7 | 60.2 | n.d. |
| 1 hr | 4.9 | 15 | 26.1 | 8.6 | 17.3 | 33.9 | 19.5 | 199.9 | n.d. | 58.9 | 126.2 | 20 | 24.1 | 39.7 | 21.1 | n.d. |
| 1.5 hr | n.d. | n.d. | n.d. | n.d. | n.d. | n.d. | n.d. | n.d. | n.d. | n.d. | n.d. | n.d. | n.d. | n.d. | n.d. | n.d. |
| 2 hr | n.d. | n.d. | n.d. | n.d. | n.d. | n.d. | n.d. | n.d. | n.d. | n.d. | n.d. | n.d. | n.d. | n.d. | n.d. | n.d. |
| 3 hr | 5.7 | 4.8 | 14.8 | 3.5 | 6.5 | 7.7 | 2.5 | 122 | n.d. | 50.2 | 125.2 | 15.6 | 11.4 | 13.3 | 4.2 | n.d. |
| 5.5 hr | 3.8 | 3.8 | 8.4 | 3.8 | 7.7 | 8.8 | 2.9 | 84.9 | n.d. | 78 | 177.8 | 17 | 9.3 | 14.5 | 5.4 | n.d. |
| 24 hr | 4.7 | 1 | 2.1 | 0.6 | 2.5 | 2.1 | 0.5 | 19 | n.d. | 90.7 | 267.5 | 15.9 | 6.7 | 8.5 | 4 | n.d. |
| 48 hr | n.d. | n.d. | n.d. | n.d. | n.d. | n.d. | n.d. | n.d. | n.d. | n.d. | n.d. | n.d. | n.d. | n.d. | n.d. | n.d. |
| 168 hr | 0.19 | 0.005 | 0.003 | 0 | 0 | 0.002 | 0 | 0 | n.d. | n.d. | n.d. | n.d. | n.d. | n.d. | n.d. | n.d. |
| | modified fusion protein produced in BHK cells (galactosylated) | | | | | | | | | | | | | | | |
| | μg galactosylated fusion protein/g of tumor or/g of organ measured in an OFAT | | | | | | | | μg of β-glucuronidase/g of tumor or/g of organ measured in an EAT | | | | | | |
| | tumor | spleen | liver | intestine | kidney | lung | heart | plasma | tumor | spleen | liver | gut | kidney | lung | heart | plasma |
| 0.05 hr | 1.6 | 7.1 | 51.9 | 2.15 | 7.78 | 21.6 | 15.7 | 83.3 | n.d. | 35.5 | 75.1 | 14 | 13 | 39 | 17.9 | n.d. |
| 1 hr | 0.5 | 0.19 | 1.9 | 0.29 | 1.16 | 0.26 | 0.17 | 0.06 | n.d. | 27.6 | 167.5 | 17.4 | 5.5 | 7.2 | 1.4 | n.d. |

TABLE 6-continued

Pharmacokinetic comparison between unmodified and modified humanized two-chain fusion proteins in CD-1 nude mice bearing a human tumor xenograft (MzSto1)

|  | tumor | spleen | liver | intestine | kidney | lung | heart | plasma | tumor | spleen | liver | gut | kidney | lung | heart | plasma |
|---|---|---|---|---|---|---|---|---|---|---|---|---|---|---|---|---|
| 1.5 hr | n.d. | n.d. | n.d. | n.d. | n.d. | n.d. | n.d. | n.d. | n.d. | n.d. | n.d. | n.d. | n.d. | n.d. | n.d. | n.d. |
| 2 hr | n.d. | n.d. | n.d. | n.d. | n.d. | n.d. | n.d. | n.d. | n.d. | n.d. | n.d. | n.d. | n.d. | n.d. | n.d. | n.d. |
| 3 hr | 0.16 | 0.27 | 0.09 | 0.03 | 0 | 0.3 | 0 | 0 | n.d. | 23.8 | 132.7 | 8.9 | 4.4 | 6.3 | 0.86 | n.d. |
| 5.5 hr | 0.27 | 0.02 | 0.11 | 0.05 | 0.02 | 0.08 | 0 | 0 | n.d. | 28.3 | 164.5 | 10.7 | 4.1 | 6 | 1.1 | n.d. |
| 24 hr | 0.05 | 0.02 | 0.04 | 0 | 0 | 0 | 0 | 0 | n.d. | 31.5 | 126.2 | 12.8 | 4.7 | 5.6 | 1.4 | n.d. |
| 48 hr | n.d. | n.d. | n.d. | n.d. | n.d. | n.d. | n.d. | n.d. | n.d. | n.d. | n.d. | n.d. | n.d. | n.d. | n.d. | n.d. |
| 168 hr | n.d. | n.d. | n.d. | n.d. | n.d. | n.d. | n.d. | n.d. | n.d. | n.d. | n.d. | n.d. | n.d. | n.d. | n.d. | n.d. | modified fusion protein produced in BHK cells (desialylated)

| | μg desialylated fusion protein/g of tumor or/g of organ measured in an OFAT | | | | | | | | μg of β-glucuronidase/g of tumor or/g of organ measured in an EAT | | | | | | | |
|---|---|---|---|---|---|---|---|---|---|---|---|---|---|---|---|---|
|  | tumor | spleen | liver | intestine | kidney | lung | heart | plasma | tumor | spleen | liver | gut | kidney | lung | heart | plasma |
| 0.05 hr | 1.3 | 14.6 | 38.9 | 10.2 | 20.6 | 49.8 | 24.2 | 234.9 | 1.3 | 43.2 | 63.2 | 48.7 | 23.8 | 56.1 | 25.7 | 250 |
| 1 hr | n.d. | n.d. | n.d. | n.d. | n.d. | n.d. | n.d. | n.d. | n.d. | n.d. | n.d. | n.d. | n.d. | n.d. | n.d. | n.d. |
| 1.5 hr | n.d. | n.d. | n.d. | n.d. | n.d. | n.d. | n.d. | n.d. | n.d. | n.d. | n.d. | n.d. | n.d. | n.d. | n.d. | n.d. |
| 2 hr | n.d. | n.d. | n.d. | n.d. | n.d. | n.d. | n.d. | n.d. | n.d. | n.d. | n.d. | n.d. | n.d. | n.d. | n.d. | n.d. |
| 3 hr | 3.3 | 1.1 | 2.8 | 0.37 | 1.5 | 1.8 | 1.3 | 13.8 | 3.3 | 69.8 | 199.2 | 9.2 | 7.4 | 6.1 | 3.9 | 13.5 |
| 5.5 hr | 2.9 | 0.1 | 0.22 | 0.02 | 0.04 | 0.19 | 0.06 | 0.65 | 2.9 | 68.7 | 342.1 | 10.6 | 4 | 4.1 | 2.5 | 0.76 |
| 24 hr | 0.4 | 0.1 | 0.04 | 0.002 | 0.004 | 0.16 | 0.001 | 0.004 | 0.4 | 179 | 641.1 | 34.6 | 15.8 | 16.9 | 7 | 0.058 |
| 48 hr | 0.1 | 0 | 0.04 | 0 | 0 | 0.55 | 0 | 0 | 0.1 | 185.9 | 639.7 | 32.7 | 8.8 | 21 | 12.7 | 0.013 |
| 168 hr | n.d. | n.d. | n.d. | n.d. | n.d. | n.d. | n.d. | n.d. | n.d. | n.d. | n.d. | n.d. | n.d. | n.d. | n.d. | n.d. |

TABLE 7

Pharmacokinetic comparison between unmodified and modified humanized two-chain fusion proteins in CD-1 nude mice bearing a human tumor xenograft (LoVo)

unmodified fusion protein produced in BHK cells

| | μg fusion protein/g of tumor or/g of organ measured in an OFAT | | | | | | | | μg of β-glucuronidase/g of tumor or/g of organ measured in an EAT | | | | | | | |
|---|---|---|---|---|---|---|---|---|---|---|---|---|---|---|---|---|
|  | tumor | spleen | liver | intestine | kidney | lung | heart | plasma | tumor | spleen | liver | gut | kidney | lung | heart | plasma |
| 0.05 hr | 0.86 | 13.5 | 56.8 | 1.9 | 7.6 | 15.5 | 3.4 | 602 | n.d. | 42.8 | 96.5 | 12.5 | 12.4 | 21.6 | 3.9 | n.d. |
| 1 hr | n.d. | 7.9 | 25.2 | 2.7 | 3.9 | 10.9 | 2.6 | 171.7 | n.d. | 57.2 | 202.6 | 10.7 | 8.4 | 15.5 | 9.2 | n.d. |
| 1.5 hr | 4.05 | 7.3 | 19.5 | 3.3 | 10.3 | 23.9 | 14.2 | 138 | n.d. | 51.5 | 164.6 | 12.3 | 16.1 | 30.6 | 6.8 | n.d. |
| 2 hr | n.d. | 5.4 | 15.1 | 2.5 | 4.8 | 7.9 | 1.9 | 119 | n.d. | 59.5 | 136.9 | 12 | 8.6 | 12.9 | 5.4 | n.d. |
| 3 hr | 1.8 | 4.9 | 12.4 | 3 | 8.5 | 17.3 | 9.2 | 105 | n.d. | 51.9 | 181 | 14.1 | 13.1 | 23.4 | 8.9 | n.d. |
| 5.5 hr | n.d. | n.d. | n.d. | n.d. | n.d. | n.d. | n.d. | n.d. | n.d. | n.d. | n.d. | n.d. | n.d. | n.d. | n.d. | n.d. |
| 24 hr | n.d. | n.d. | n.d. | n.d. | n.d. | n.d. | n.d. | n.d. | n.d. | n.d. | n.d. | n.d. | n.d. | n.d. | n.d. | n.d. |
| 48 hr | n.d. | n.d. | n.d. | n.d. | n.d. | n.d. | n.d. | n.d. | n.d. | n.d. | n.d. | n.d. | n.d. | n.d. | n.d. | n.d. |
| 168 hr | 0.409 | n.d. | n.d. | n.d. | n.d. | n.d. | n.d. | 0.023 | n.d. | n.d. | n.d. | n.d. | n.d. | n.d. | n.d. | n.d. | modified fusion protein produced in BHK cells (galactosylated)

| | μg galactosylated fusion protein/g of tumor or/g of organ measured in an OFAT | | | | | | | | μg of β-glucuronidase/g of tumor or/g of organ measured in an EAT | | | | | | | |
|---|---|---|---|---|---|---|---|---|---|---|---|---|---|---|---|---|
|  | tumor | spleen | liver | intestine | kidney | lung | heart | plasma | tumor | spleen | liver | gut | kidney | lung | heart | plasma |
| 0.05 hr | 0.45 | 6.3 | 41.2 | 1.43 | 2.78 | 7.7 | 0.82 | 257.6 | n.d. | 29.3 | 48.2 | 12.4 | 8.2 | 14.1 | 1.7 | n.d. |
| 1 hr | n.d. | 0.16 | 0.63 | 0.05 | 0.03 | 0.033 | 0 | 0.032 | n.d. | 24.6 | 132.1 | 13.1 | 4.6 | 5.2 | 0.95 | n.d. |
| 1.5 hr | 1.45 | 0.09 | 0.42 | 0.05 | 0.05 | 0.164 | 0.036 | 0.006 | n.d. | 19.6 | 120.8 | 15.3 | 4.2 | 4.7 | 1.7 | n.d. |
| 2 hr | n.d. | 0.008 | 0.11 | 0.03 | 0 | 0.1 | 0 | 0 | n.d. | 10.7 | 111.4 | 16.6 | 3.6 | 5.6 | 0.88 | n.d. |
| 3 hr | 0.48 | 0 | 0.08 | 0.006 | 0 | 0.05 | 0.002 | 0 | n.d. | 22 | 164.9 | 13.6 | 3.8 | 4.9 | 0.95 | n.d. |
| 5.5 hr | n.d. | n.d. | n.d. | n.d. | n.d. | n.d. | n.d. | n.d. | n.d. | n.d. | n.d. | n.d. | n.d. | n.d. | n.d. | n.d. |
| 24 hr | n.d. | n.d. | n.d. | n.d. | n.d. | n.d. | n.d. | n.d. | n.d. | n.d. | n.d. | n.d. | n.d. | n.d. | n.d. | n.d. |
| 48 hr | n.d. | n.d. | n.d. | n.d. | n.d. | n.d. | n.d. | n.d. | n.d. | n.d. | n.d. | n.d. | n.d. | n.d. | n.d. | n.d. |
| 168 hr | n.d. | n.d. | n.d. | n.d. | n.d. | n.d. | n.d. | n.d. | n.d. | n.d. | n.d. | n.d. | n.d. | n.d. | n.d. | n.d. |

TABLE 8

Pharmacokinetic comparison between unmodified humanized two-chain fusion proteins, produced in BHK cells and CHO cells, in CD-1 nude mice bearing a human tumor xenograft (MzSto1)

| | tumor | spleen | liver | intestine | kidney | lung | heart | plasma |
|---|---|---|---|---|---|---|---|---|
| unmodified fusion protein produced in BHK cells | | | | | | | | |
| μg of fusion protein/g of tumor or/g of organ measured in an OFAT | | | | | | | | |
| 0.05 hr | 3.807 | 22.779 | 44.411 | 7.732 | 27.792 | 53.59 | 33.941 | 413 |
| 3 hr | 6.166 | 8.847 | 20.099 | 4.125 | 12.609 | 26.363 | 12.93 | 147 |
| 24 hr | 4.944 | 0.935 | 1.416 | 0.249 | 1.315 | 2.779 | 1.493 | 12.3 |
| 72 hr | 0.818 | 0.094 | 0.14 | 0.058 | 0.112 | 0.241 | 0.136 | 1.152 |
| 168 hr | 0.314 | 0.002 | 0.005 | 0.002 | 0.002 | 0.008 | 0 | 0.015 |
| μg of β-glucuronidase/g of tumor or/g of organ measured in an EAT | | | | | | | | |
| 0.05 hr | 6.473 | 27.927 | 44.748 | 13.045 | 27.419 | 59.345 | 30.897 | n.d. |
| 3 hr | 9.982 | 70.009 | 445.32 | 15.714 | 16.415 | 27.014 | 14.427 | n.d. |
| 24 hr | 28.384 | 41.799 | 33.834 | 6.605 | 2.422 | 3.99 | 2.498 | n.d. |
| 72 hr | 9.929 | 20.458 | 12.391 | 12.416 | 1.051 | 2.283 | 1.306 | n.d. |
| 168 hr | 7.423 | 7.393 | 6.083 | 5.164 | 0.94 | 1.483 | 0.502 | n.d. |
| unmodified fusion protein produced in CHO cells | | | | | | | | |
| μg of fusion protein/g of tumor or/g of organ measured in an OFAT | | | | | | | | |
| 0.05 hr | 3.583 | 19.179 | 33.392 | 7.96 | 23.089 | 61.279 | 24.018 | 308 |
| 3 hr | 6.526 | 8.555 | 17.787 | 7.098 | 11.613 | 26.755 | 10.824 | 157.9 |
| 24 hr | 4.668 | 1.002 | 1.225 | 0.299 | 1.218 | 2.926 | 1.361 | 12.082 |
| 72 hr | 2.176 | 0.036 | 0.028 | 0.013 | 0.023 | 0.059 | 0.029 | 0.144 |
| 168 hr | 0.653 | 0.003 | 0.002 | 0.003 | 0 | 0.003 | 0 | 0.005 |
| μg of β-glucuronidase/g of tumor or/g of organ measured in an EAT | | | | | | | | |
| 0.05 hr | 6.475 | 23.883 | 29.696 | 14 | 23.223 | 56.864 | 23.042 | n.d. |
| 3 hr | 10.96 | 89.594 | 204.82 | 15.928 | 13.66 | 26.994 | 12.556 | n.d. |
| 24 hr | 29.279 | 72.999 | 23.754 | 7.011 | 2.513 | 5.003 | 3.089 | n.d. |
| 72 hr | 50.13 | 25.828 | 7.527 | 7.613 | 1.542 | 2.568 | 1.719 | n.d. |
| 168 hr | 5.515 | 14.251 | 4.172 | 4.172 | 1.202 | 1.588 | 1.193 | n.d. |

Example 6

Galactosylation of the Two-Chain Fusion Protein

The galactosylation of the fusion protein was carried out using a modification of the method of Mattes (*J. Natl. Cancer Inst.*, 79: 855 (1987) which is incorporated herein in its entirety):

Cyanomethyl-2,3,4,6-tetra-0-acetyl-1-thio-β-D-galactopyranoside (Sigma; 250 mg) was dissolved in dried methanol (Merck; 6.25 ml), and 625 μl of a methanolic sodium methoxide solution (5.4 mg/ml) were then pipetted in. After incubating at room temperature for 48 h, an aliquot of 5 ml of the activated galactose derivative was removed and the methanol evaporated off in a stream of nitrogen 100 ml of a fusion protein solution (1 mg/ml in 0.25 M sodium borate buffer, pH 8.5) were added to the remaining residue, and the mixture incubated at R.T. for 24 h. This was followed by dialysis overnight against PBS.

Galactosylation of the preformed BW 431/26-*E. coli* β-glucuronidase conjugates and the monoclonal antibody BW 431/26 was carried out in a similar manner. Using similar chemistry, lactosilation, N-acetyl-lactosilation and glucosilation of AEC and FUP can be performed.

Example 7

Working Up Organs/Tumors for FUP Determination

The following sequential steps were carried out:
1. Nude mice (CD1), which possess a subcutaneous tumor and which have been treated with fusion protein or antibody-enzyme conjugate, are bled retroorbitally and then sacrificed.
2. The blood is immediately added to an Eppendorf tube which already contains 10 μl of Liquemin 25000 (from Hoffman LaRoche AG).
3. The treated blood from 2. above is centrifuged (in a Megafuge 1.0 centrifuge, from Heraeus) at 2500 rpm for 10 min; the plasma is then isolated and frozen down until testing.
4. The organs, or the tumor, are removed, weighed and then completely homogenized with 2 ml of 1% BSA in PBS, pH 7.2.
5. The tumor homogenates are adjusted to pH 4.2 with 0.1N HCl (the sample must not be overtitrated, or the β-glucuronidase will be activated prematurely at pH<3.8!)
6. Homogenates are centrifuged at 16000 g for 30 min; the clear supernatant fluids are removed and neutralized with 0.1 N NaOH.
7. The supernatants and the plasma can now be tested in an OFAT (measures FUP concentration) or an EAT (measures β-glucuronidase concentration), as described in the examples below.

Example 8

OFAT (Organ Fusion Protein Activity Test)

The test proceeds in the following manner:
1. 75 μl of a goat anti-human-kappa antibody (from Southern Biotechnology Associates, Order No. 2060-01), diluted 1:300 in PBS, pH 7.2, are added to each well of a microtitration plate (polystyrene U form, type B, from Nunc, Order No. 4-60445).
2. The microtitration plates are covered and incubated at room temperature overnight.

3. The microtitration plates are then washed 3 times with 250 μl of 0.05 M Tris-citrate buffer, pH 7.4, per well.
4. These microtitration plates, which have been coated in this manner, are incubated with 250 μl of blocking solution (1% casein in PBS, pH 7.2) per well at room temperature for 30 mins (blocking of non-specific binding sites)
   (coated microtitration plates which are not required are dried at room temperature for 24 hours and then sealed, together with desiccator cartridges, in coated aluminium bags for long-term storage).
5. The substrate is prepared while the blocking is proceeding (fresh substrate for each test: 2.5 mM 4-methylumbelliferyl β-D-glucuronide, Order No.: M-9130, from Sigma, in 200 mM Na acetate+0.01% BSA, pH 4.5).
6. Thereafter, 10 samples+1 positive control+1 negative control are diluted in 1% casein in PBS, pH 7.2, 1:2 in 8 steps (starting from 150 μl of sample, 75 μl of sample are pipetted into 75 μl of casein recipient solution, etc.) in an untreated 96-well U-shape bottomed microtiter plate (polystyrene, from Renner, Order. No. 12058).
7. The blocking solution is sucked off from the microtitration plate coated with anti-human-kappa antibody, and 50 μl of the diluted samples are transferred to each well of the test plate from the dilution plate, and the test plate is incubated at room temperature for 30 min.
8. The test plate is washed 3 times with ELISA washing buffer (Behringwerke, Order No. OSEW96);
9. 50 μl of substrate are applied per well and the test plates are covered and incubated at 37° C. for 2 h.
10. 150 μl of stock solution (0.2 M glycine+0.2% SDS, pH 11.7) are then added to each well.
11. Fluorometric evaluation is carried out in a Fluoroscan II (ICN Biomedicals, Cat. No. 78-611-00) at an excitation wavelength of 355 nm and an emission wavelength of 460 nm.
12. With the aid of the fluorescence values for the positive control (dilution series with purified fusion protein as the standard curve) included in the identical experiment, the unknown concentration of fusion protein is determined in the sample.

Example 9

EAT (Enzyme Activity Test)

The test is carried out in the following manner:
1. 10 samples+1 positive control+1 negative control are diluted 1:2 in 1% casein in PBS, pH 7.2, in 8 dilution steps in a 96-well microtiter plate (polystyrene, from Renner, Order No. 12058) so that each well contains 50 μl of sample.
2. 50 μl of substrate (2.5 mM 4-methylumbelliferyl β-D-glucuronide (from Sigma, Order No. M-9130, in 200 mM Na acetate+0.01% BSA, pH 4.5) are added to each well.
3. The microtiter plate is covered and incubated at 37° C. for 2 h.
4. 150 μl of stock solution (0.2 M glycine+0.2% SDS, pH 11.7) are then added per well.
5. Fluorometric evaluation is carried out in a Fluoroscan II (ICN Biomedicals, Cat. No. 78-611-00) at an excitation wavelength of 355 nm and an emission wavelength of 460 nm;

6. With the aid of the positive control (dilution series with purified fusion protein as the standard curve) which has been included, the sample concentrations can now be calculated.

Example 10

Desialylation of the Two-chain Fusion Glycoprotein

The two-chain fusion protein was desialylated according to Murray (*Methods in Enzymology* 149: 251 (1987)). Eight units of neuraminidase (Sigma, type X-A from *Clostridium perfringens*) coupled to agarose were washed 3× with 40 ml of 100 mM sodium acetate buffer, pH 5, and then taken up as a 1:1 suspension. One hundred milliliters of two-chain fusion protein (1 mg/ml in sodium acetate buffer, pH 5) were added to this suspension, which was then incubated with gentle shaking at 37° C. for 4 h. The immobilized neuraminidase was removed by centrifuging off, and the fusion protein was dialyzed overnight against PBS.

Example 11

Demonstrating Rapid Elimination of Modified FUP 100 mg of humanized two-chain fusion glycoprotein were purified from BHK transfectant supernatant, as described in EP-A-0 501 215, pages 10-11. The purified protein was galactosylated or desialylated, as described in the preceding examples.

400 μg of the modified protein thus obtained, in this case the galactosylated humanized two-chain fusion protein, were injected i.v. into nude mice. The mice had been injected subcutaneously, 10 days previously, with $10^6$ CEA-expressing human stomach carcinoma cells (Mz-Sto-1). At various time intervals, the mice were killed, and the concentration of functionally active modified protein was determined in the tumor, the plasma and the normal tissues using the OFAT or the EAT (see Examples 7, 8 and 9).

Nude mice which in each case had been provided with $1 \times 10^6$ CEA-negative human tumors (Oat-75) were used as the antigen control. In addition, identical quantities of the humanized two-chain fusion protein (starting protein) or of a humanized two-chain fusion protein sample which had been treated with solid phase neuraminidase (desialylated protein) were injected i.v. as the protein control (see Example 10). The quantities of the functionally active proteins found in the organs in this representative experiment are given in Tables 6 and 7.

Comparable results were found in the identical animal model system using the example of a CEA-positive colon carcinoma, a CEA-positive rectal carcinoma, a CEA-positive adenocarcinoma of the lung, a CEA-positive pancreatic carcinoma, a CEA-positive thyroid gland carcinoma, and a CEA-positive mammary carcinoma.

Therapeutic effects which are superior to those of the standard chemotherapy can be achieved when suitable non-toxic prodrugs, e.g. those described in EP-A-0 511 917, are used which are applied at a point in time at which the modified proteins have been largely eliminated from the plasma or have been internalized and degraded in the normal tissues. These effects can be improved still further by adding large quantities of galactose to the relevant modified protein, leading to optimization of the pharmacokinetics.

Further improvements can be achieved in accordance with the method described by Jahde et al, (*Cancer Res.* 52: 6209 (1992)) by adding glucose, phosphate ions or metaiodobenzylguanidine to the relevant modified protein, or injecting these compounds prior to the protein. This method leads to a decline in the pH within the tumor. This results in more efficient catalysis of the prodrugs by the enzymes used in the modified and non-modified proteins according to the invention. Alternatively, $HCO_3$— can also be employed for lowering the pH in the tumor (Gullino et al., *J. Nat. Cancer Inst.* 34: 857, (1965)).

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application P 43 14 556.6 for which benefit under 35 USC §119 is claimed, is expressly incorporated herein in its entirety.

What is claimed is:

1. A compound comprising a modified carbohydrate complement and a humanized two-chain fusion protein composed of a humanized $V_H C_{H1}$-hinge-S-human β-glucuronidase chain and of a humanized $V_L C_L$ chain, which binds specifically to an epitope of a tumor-specific antigen, wherein the modified carbohydrate complement is achieved by chemical qalactosvlation or neuraminidase treatment, wherein the modified carbohydrate complement comprises at least one exposed carbohydrate residue selected from the group consisting of galactose, mannose, N-acetylglucosamine, fucose, N-acetyllactose, glucose, and N-acetylneuraminic acid, wherein said compound has been synthesized in CHO cells, wherein the CHO cells have been selected for a higher level of glycoprotein expression, a higher rate of elimination of glycoprotein from plasma, a higher rate of concentration of the glycoprotein at the tumor-specific antigen and a higher content of high mannose type structures as compared to BHK cells which express said humanized two-chain fusion protein with a different carbohydrate complement, and wherein S is a polypeptide spacer.

2. The compound as claimed in claim 1, wherein said compound binds to a tumor cell marker comprising a tumor associated antigen selected from the group consisting of CEA, N-CAM, N-cadherin, PEM, GICA, TAG-72, TFβ, GM3, GD3, GM2, GD2, GT3, HMWMAA, pMel17, gp1 13 (Mucl8), p53, p97, MAGE-1, gp105, erbB2, EGF-R, PSA, transferrin-R, P-glycoprotein and cytokeratin.

3. A pharmaceutical preparation containing the compound according to claim 1 in a pharmaceutically acceptable vehicle.

4. A pharmaceutical preparation containing the compound according to claim 1, and an agent capable of lowering the pH in a tumor to be treated, in a pharmaceutically acceptable vehicle.

5. A pharmaceutical preparation, containing the compound according to claim 1, and galactose, in a pharmaceutically acceptable vehicle.

6. The compound of claim 1, wherein the modified carbohydrate complement is achieved by additional chemical galactosylation.

* * * * *

```
                          SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 1:

ACCAGAAGCT TATGAATATG CAAATC                                         26

(2) INFORMATION FOR SEQ ID NO: 2:

(i) SEQUENCE CHARACTERISTICS:
           (A) LENGTH: 58 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 2:

GCCACCCGAC CCACCACCGC CCGATCCACC GCCTCCTGAG GAGACGGTGA CCGTGGTC      58

(2) INFORMATION FOR SEQ ID NO: 3:

(i) SEQUENCE CHARACTERISTICS:
           (A) LENGTH: 60 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 3:

GGTGGATCGG GCGGTGGTGG GTCGGGTGGC GGCGGATCTG ACATCCAGCT GACCCAGAGC    60

(2) INFORMATION FOR SEQ ID NO: 4:

(i) SEQUENCE CHARACTERISTICS:
           (A) LENGTH: 50 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 4:

TGCAGGATCC AACTGAGGAA GCAAAGTTTA AATTCTACTC ACCTTTGATC               50
```

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

TTTTTAAGCT TAGATCTCCA CCTTGGTC        28

(2) INFORMATION FOR SEQ ID NO: 6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

AAAAAGATCT CCGCGTCTGG CGGGCCACAG TTACGTGTAG AAACCCCA        48

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GCTTCTAGAT CATTGTTTGC CTCCCTG        27